(12) United States Patent
Junker et al.

(10) Patent No.: US 7,678,935 B2
(45) Date of Patent: Mar. 16, 2010

(54) ESTERS OF PENTAHYDROXYHEXYLCARBAMOYL ALKANOIC ACIDS

(75) Inventors: Bernd Junker, Frankfurt (DE); Javier Manero, Frankfurt (DE)

(73) Assignee: Sanofi-Aventis Deutschland GmbH (DE)

( * ) Notice: Subject to any disclaimer, the term of this patent is extended or adjusted under 35 U.S.C. 154(b) by 0 days.

(21) Appl. No.: 12/271,236

(22) Filed: Nov. 14, 2008

(65) Prior Publication Data

US 2009/0082589 A1 Mar. 26, 2009

Related U.S. Application Data

(63) Continuation of application No. 11/767,298, filed on Jun. 22, 2007, now abandoned.

(51) Int. Cl.
C07C 69/96 (2006.01)
C07C 69/76 (2006.01)
(52) U.S. Cl. .......................... 558/275; 560/81
(58) Field of Classification Search ................ None
See application file for complete search history.

(56) References Cited

U.S. PATENT DOCUMENTS

| 4,596,789 | A | * | 6/1986 | Dutta et al. ............... 514/18 |
|---|---|---|---|---|
| 5,656,624 | A | | 8/1997 | Vaccaro et al. |
| 5,756,470 | A | | 5/1998 | Yumibe et al. |
| 5,846,966 | A | | 12/1998 | Rosenblum et al. |
| 5,889,002 | A | | 3/1999 | Nielsen et al. |
| 6,225,310 | B1 | | 5/2001 | Nielsen et al. |
| 6,268,343 | B1 | | 7/2001 | Knudsen et al. |
| 6,525,083 | B2 | | 2/2003 | Acton, III et al. |
| 6,992,067 | B2 | | 1/2006 | Glombik et al. |
| 7,067,689 | B1 | | 6/2006 | Renze et al. |
| 7,205,290 | B2 | | 4/2007 | Jaehne et al. |
| 2007/0197498 | A1 | | 8/2007 | Jaehne et al. |
| 2008/0281092 | A1 | | 11/2008 | Glombik et al. |
| 2009/0203578 | A1 | | 8/2009 | Wollmann et al. |

FOREIGN PATENT DOCUMENTS

| WO | WO 97/16455 A1 | 5/1997 |
|---|---|---|
| WO | WO 97/26265 A1 | 7/1997 |
| WO | WO 97/41097 A2 | 11/1997 |
| WO | WO 97/45406 A1 | 12/1997 |
| WO | WO 98/08871 A1 | 3/1998 |
| WO | WO 99/03861 A1 | 1/1999 |
| WO | WO 00/63703 A1 | 10/2000 |

OTHER PUBLICATIONS

Non-Final Office Action for U.S. Appl. No. 10/021,502 (U.S. Patent No. 6,992,067) mailed on Sep. 10, 2003, 4 pages.
Final Office Action for U.S. Appl. No. 10/021,502 (U.S. Patent No. 6,992,067) mailed on Apr. 16, 2004, 11 pages.
Non-Final Office Action for U.S. Appl. No. 10/021,502 (U.S. Patent No. 6,992,067) mailed on Aug. 25, 2004, 5 pages.
Non-Final Office Action for U.S. Appl. No. 10/021,502 (U.S. Patent No. 6,992,067) mailed on Feb. 8, 2005, 9 pages.
Notice of Allowance for U.S. Appl. No. 10/021,502 (U.S. Patent No. 6,992,067) mailed on Jul. 12, 2005, 4 pages.
Non-Final Office Action for U.S. Appl. No. 10/813,954 (U.S. Patent No. 7,205,290) mailed on May 18, 2006, 7 pages.
Notice of Allowance for U.S. Appl. No. 10/813,954 (U.S. Patent No. 7,205,290) mailed on Nov. 27, 2006, 4 pages.
Non-Final Office Action for U.S. Appl. No. 11/155,109 mailed on Dec. 3, 2008, 9 pages.
Notice of Allowance for U.S. Appl. No. 12/219,196 (U.S. patent publication 2008-0281092) mailed on Apr. 6, 2009, 5 pages.
U.S. Appl. No. 12/269,802 of T. Wollmann, R. Duffy, and F. Cullmann filed Nov. 12, 2008.
U.S. Appl. No. 11/767,284, filed Jun. 22, 2007, Haubrich et al.
Castañer, R. M., "Ezetimbe, Hypolipidemic Cholesterol Absorption Inhibitor SCH-58235," *Drugs of the Future* 2000, 25(7):679-685.
Chaudhary, A., et al., "$CO_2$ Offgas as a Mechanistic Probe and Scale-up Tool in N-Acylations Using Mixed Anhydrides from Amino Acids and Isobutyl Chloroformate," *Organic Process Research & Development* (2003) 7: 888-895.
Goodman and Gilman's *The Pharmacological Basis of Therapeutics*, 10th Ed., 2001, p. 54.
Greene, T., et al., *Protective Groups in Organic Synthesis*, John Wiley & Sons, Inc. (1999), 3rd Ed., including: (a) "The Role of Protective Groups in Organic Synthesis," pp. 1, 4, and 5; (b) "Protection for the Carboxyl Group," pp. 372-373; (c) "Formation of Esters," pp. 373-374; (d) "Methyl Ester," pp. 383-387; (e) "Benzyl Ester," pp. 415-419; (f) "Reactivities Reagents, and Reactivity Charts," pp. 701-702; (g) "Reactivity Charts," pp. 705-707; and (h) "Reactivity Chart 6. Protection for the Carboxyl Group," pp. 728-731.

(Continued)

Primary Examiner—Paul A Zucker
(74) Attorney, Agent, or Firm—Finnegan, Henderson, Farabow, Garrett & Dunner

(57) ABSTRACT

Provided are compounds of formula A and formula I:

A compound of formula A:

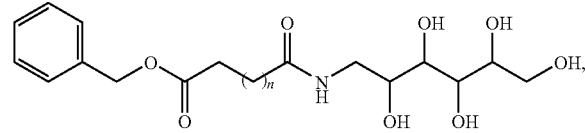

wherein n is an integer from 6 to 17 and
a compound of formula I:

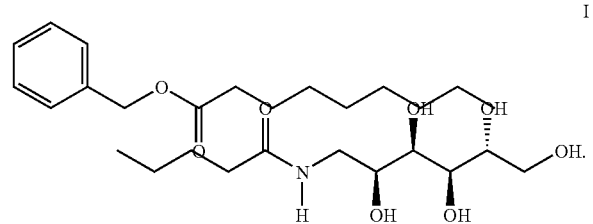

3 Claims, No Drawings

OTHER PUBLICATIONS

Kosoglou, T., et al., "Coadministration of Simvastatin and Ezetimibe Leads to Significant Reduction in LDL-Cholesterol," Proceedings of the 3rd International Congress on Coronary Artery Disease: From Prevention to Intervention, 2000, p. 275.
Prata, C. A. H., et al., "Charge-Reversal Amphiphiles for Gene Delivery," *J. Am. Chem. Soc.* (2004) 126:12196-12197.
Prata, C. A. H., et al., Supporting Information for "Charge-Reversal Amphiphiles for Gene Delivery," *J. Am. Chem. Soc.* (2004) 126:12196-12197.
Saitoh, M., et al., "Convenient Selective Monoesterification of α,ω-Dicarboxylic Acids Catalyzed by Ion-Exchange Resins," *Tetrahedron Letters*, 1996, vol. 37, No. 37, pp. 6733-6736.
Vaccaro, W. D., et al., "Sugar-Substituted 2-Azetidinone As Cholesterol Absorption Inhibitors," *Biorganic & Medicinal Chemistry Letters* 8(1998):35-40.
Vaccaro, W. D., et al., "Sugar-Substituted 2-Azetidinone Cholesterol Absorption Inhibitors: Enhanced Potency by Modification of the Sugar," *Biorganic & Medicinal Chemistry Letters* 8(1998):313-318.
van Heek, M., et al., "Comparison of the activity and disposition of the novel cholesterol absorption inhibitor, SCH58235, and its glucuronide, SCH60663," *British Journal of Pharmacology* 129:1748-1754 (2000).
Zaks, A., et al., "Enzymatic Glucuronidation of a Novel Cholesterol Absorption Inhibitor, SCH58235," *Applied Biochemistry and Biotechnology*, 73:205-214 (1998).
83 USPQ2d 1169 *Takeda Chemical Industries Ltd.* v. *Alphapharm Pty. Ltd.*, U.S. Court of Appeals Federal Circuit, No. 06-1329, Decided Jun. 28, 2007 492 F3d 1350.
87 USPQ2d 1452 *Eisai Co. Ltd.* v. *Dr. Reddy's Laboratories Ltd.*, U.S. Court of Appeals Federal Circuit, Nos. 2007-1397, 1398, Decided Jul. 21, 2008, 533 F3d 1353.
Transmittal of New Application for U.S. Appl. No. 11/155,109, filed Jun. 17, 2005, 77 pages.
Preliminary Amendment for U.S. Appl. No. 11/155,109, filed Jun. 17, 2005, 17 pages.
Preliminary Amendment for U.S. Appl. No. 11/155,109, filed Sep. 8, 2005, 15 pages.
Office Action for U.S. Appl. No. 11/155,109 mailed on Aug. 17, 2006, 11 pages.
Amendment and Remarks for U.S. Appl. No. 11/155,109, filed Dec. 5, 2006, 6 pages.
Final Office Action for U.S. Appl. No. 11/155,109 mailed on Feb. 14, 2007, 8 pages.
Request for Continued Examination and Amendment Submitted/Entered with Filing of CPA/RCE for U.S. Appl. No. 11/155,109, filed Jun. 14, 2007, 11 pages.
Office Action for U.S. Appl. No. 11/155,109 mailed on Jul. 16, 2007, 10 pages.
Amendment and Remarks for U.S. Appl. No. 11/155,109, filed Oct. 15, 2007, 7 pages.
Final Office Action for U.S. Appl. No. 11/155,109 mailed on Jan. 9, 2008, 8 pages.
Pre-Appeal Brief Request for Review for U.S. Appl. No. 11/155,109 received on Apr. 7, 2008, 8 pages.
Notice of Panel Decision from Pre-Appeal Brief Review U.S. Appl. No. 11/155,109 mailed on May 2, 2008, 3 pages.
Appeal Brief for U.S. Appl. No. 11/155,109, filed Jul. 3, 2008, 22 pages.
Examiner's Answer to Appeal Brief for U.S. Appl. No. 11/155,109 mailed on Aug. 6, 2008, 9 pages.
Request for Continued Examination and Amendment Submitted/Entered with Filing of CPA/RCE for U.S. Appl. No. 11/155,109, filed Oct. 1, 2008, 22 pages.
Transmittal of New Application for U.S. Appl. No. 11/797,720, filed May 7, 2007, 79 pages.
Preliminary Amendment for U.S. Appl. No. 11/797,720, filed May 7, 2007, 4 pages.
Office Action for U.S. Appl. No. 11/797,720 mailed on Nov. 16, 2007, 9 pages.
Amendment and Remarks for U.S. Appl. No. 11/797,720, filed Jan. 15, 2008, 6 pages.
Final Office Action for U.S. Appl. No. 11/797,720 mailed on Apr. 21, 2008, 9 pages.
Amendment and Remarks after Final Office Action for U.S. Appl. No. 11/797,720, filed Jul. 17, 2008, 3 pages.
Notice of Allowance for U.S. Appl. No. 11/797,720 mailed on Oct. 2, 2008, 23 pages.
Notice of Allowance for U.S. Appl. No. 11/177,410 mailed on Mar. 31, 2006, 4 pages.
NonFinal Office Action for U.S. Appl. No. 10/021,502 (U.S. Patent No. 6,992,067) mailed on Sep. 10, 2003, 4 pages.
Final Office Action for U.S. Appl. No. 10/021,502 (U.S. Patent No. 6,992,067) mailed on Apr. 16, 2004, 11 pages.
NonFinal Office Action for U.S. Appl. No. 10/021,502 (U.S. Patent No. 6,992,067) mailed on Aug. 25, 2004, 5 pages.
NonFinal Office Action for U.S. Appl. No. 10/021,502 (U.S. Patent No. 6,992,067) mailed on Feb. 8, 2005, 9 pages.
NonFinal Office action for U.S. Appl. No. 10/813,945 (U.S. Patent No. 7,205,290) mailed on May 18, 2006, 7 pages.
NonFinal Office Action for U.S. Appl. No. 11/155,109 mailed on Dec. 3, 2008, 9 pages.
Examiner Interview Summary for U.S. Appl. No. 11/155,109 mailed on Apr. 14, 2009, 4 pages.
Final Office Action for U.S. Appl. No. 11/155,109 mailed on Jun. 25, 2009, 9 pages.
Notice of Allowance for U.S. Appl. No. 12/219,196 mailed on Apr. 6, 2009, 5 pages.

\* cited by examiner

ESTERS OF PENTAHYDROXYHEXYLCARBAMOYL ALKANOIC ACIDS

This is application is a Continuation of U.S. patent application Ser. No. 11/767,298, filed Jun. 22, 2007 now abandoned which is incorporated herein by reference for all purposes.

Provided are certain compounds set forth below, certain processes for the preparation of esters of pentahydroxyhexylcarbamoyl alkanoic acids, and certain uses therefore.

Benzyl pentahydroxyhexylcarbamoylundecanoate has the formula I

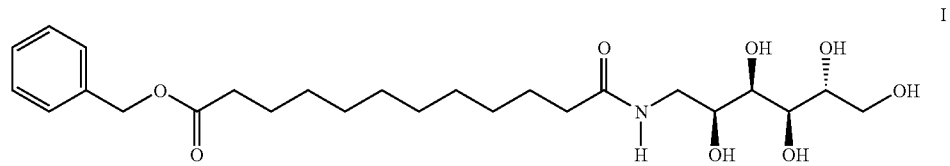

and is an intermediate in the preparation of the compound of formula II

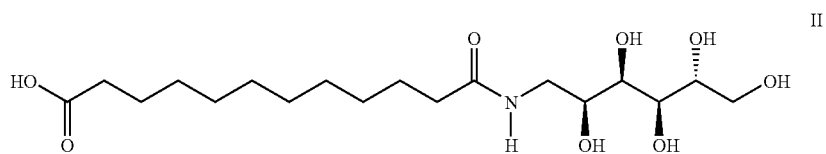

which in turn is an intermediate in the synthesis of the compound of formula III

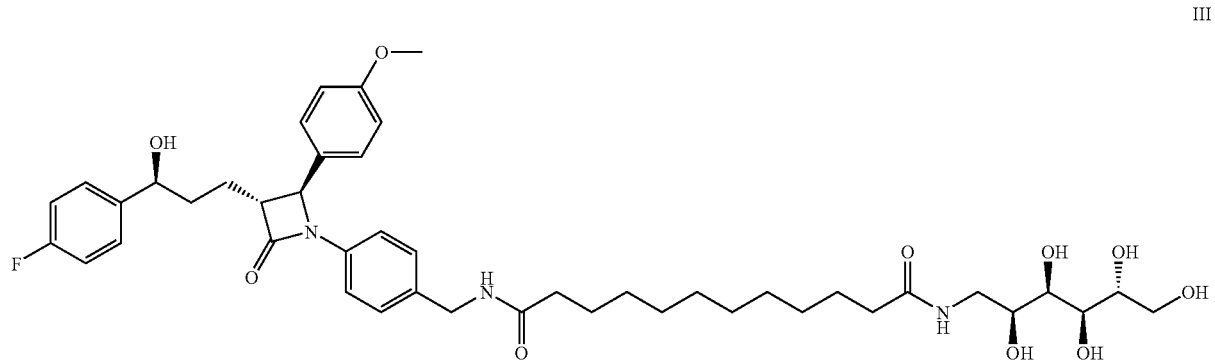

which is described in U.S. Pat. No. 7,205,290 as having, for example, cholesterol-lowering properties.

Provided generally is a process for preparing a compound of formula A

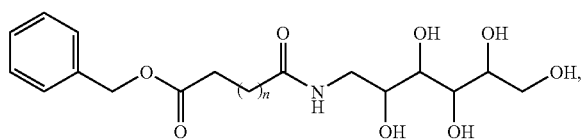

A wherein n is an integer from 6 to 17 comprising
a) reacting a compound of formula B

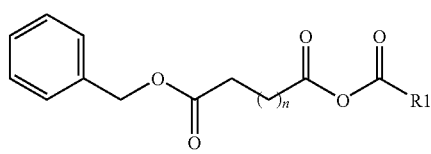

B with a compound of VI

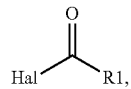

VI wherein
Hal is chosen from Br, Cl, and I, and
R1 is an alkyl radical which has from 1 to 18 carbon atoms and in which
at least one —CH$_2$— group of the alkyl radical is optionally replaced by at least one group chosen from —O—, —CO—, —CH=CH—, —C≡C—, and aryl groups, and
the alkyl radical is optionally substituted by at least one halogen chosen from F, Cl, Br, and I,
to form a compound of formula C

C and
b) reacting the compound of formula C with glucamine to form the compound of formula A.

In an exemplary embodiment is provided a process for preparing a compound of formula I

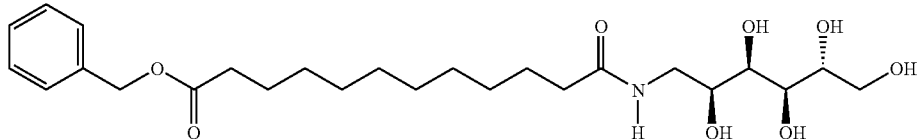

I comprising a) reacting a compound of formula IV

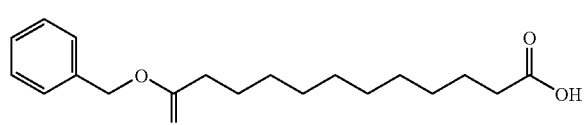

IV with a compound of formula VI

VI wherein
Hal is chosen from Br, Cl, and I, and
R1 is an alkyl radical which has from 1 to 18 carbon atoms and in which
at least one —CH$_2$— group of the alkyl radical is optionally replaced by at least one group chosen from —O—, —CO—, —CH=CH—, —C≡C—, and aryl groups, and
the alkyl radical is optionally substituted by at least one halogen chosen from F, Cl, Br, and I,
to form a compound of formula V

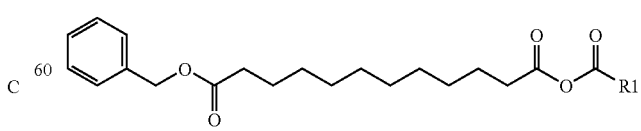

V and
b) reacting the compound of formula V with D-glucamine to form the compound of formula I.

Also provided is a process for preparing a compound of formula I

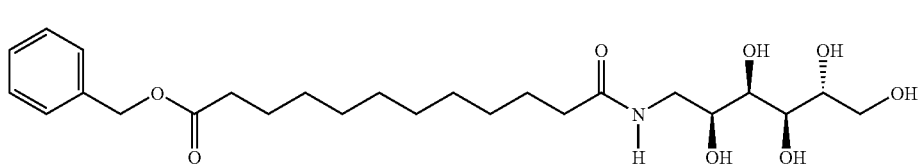

comprising a) reacting a compound of formula IV

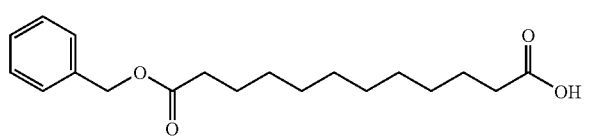

with a compound of formula VI

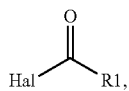

wherein Hal is chosen from Br, Cl, and I, and

R1 is an alkyl radical which has from 1 to 18 carbon atoms and in which at least one —CH$_2$— group of the alkyl radical is optionally replaced by at least one group chosen from —O—, —CO—, —CH═CH—, —C≡C—, and aryl groups, and the alkyl radical is optionally substituted by at least one halogen chosen from F, Cl, Br, and I, to form a compound of formula V

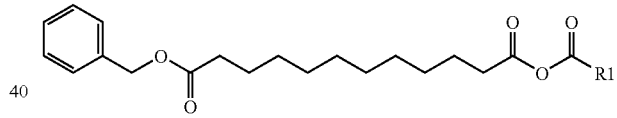

b) reacting the compound of formula V with monobenzyl ester of dodecanedioic acid of formula IV to form a compound of formula VIII

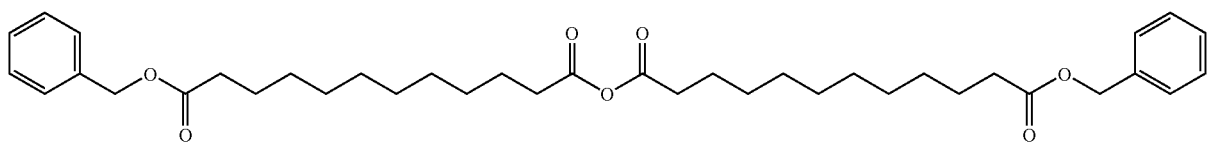

and c) reacting the compound of formula VIII with D-glucamine to form the compound of formula I.

Also provided is a process of preparing a compound of formula I

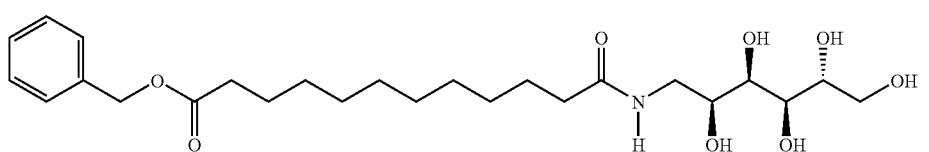

comprising converting a compound of formula V

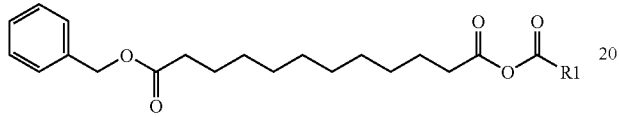

to the compound of formula I.

Also provided is a process of preparing a compound of formula I

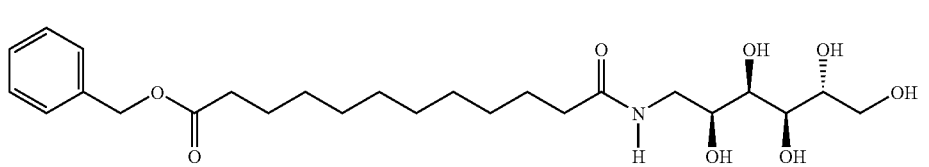

comprising converting a compound of formula Va

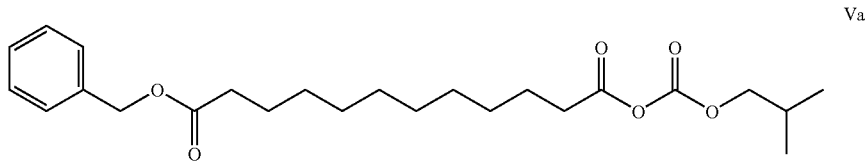

to the compound of formula I.

Also provided is a process for preparing a compound of formula Va

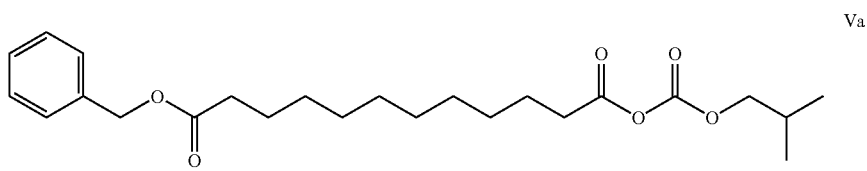

comprising reacting a compound of formula IV

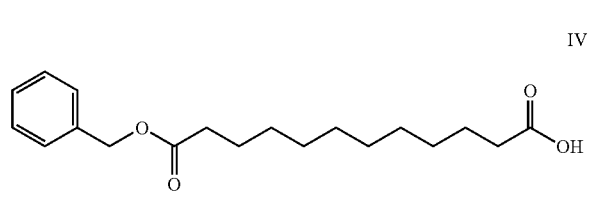

with a compound of formula VIa

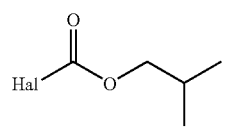

wherein Hal is chosen from Br, Cl, and I to form a compound of formula Va.

Also provided is a process for preparing a compound of formula I comprising
a) reacting a compound of formula IV

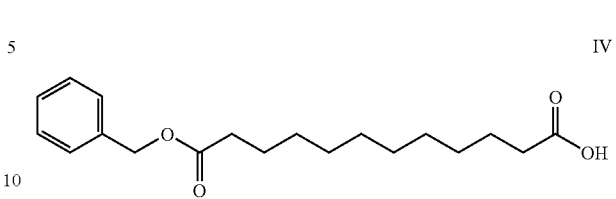

with a compound of formula VIa

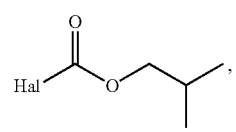

wherein Hal is chosen from Br, Cl, and I, to form a compound of formula Va

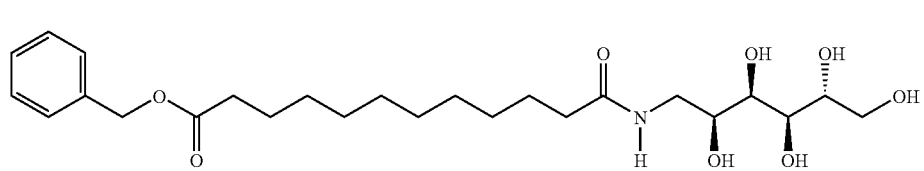

comprising reacting a compound of formula Va

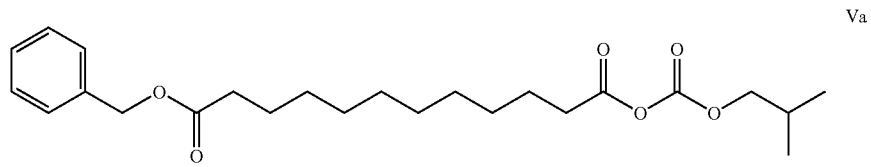

with D-glucamine to form the compound of formula I.

Also provided is a process for preparing a compound of formula VIII

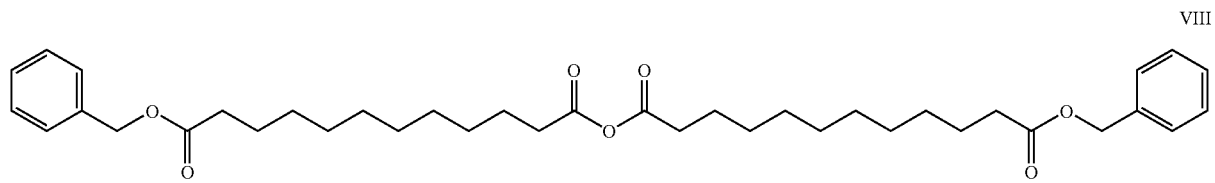

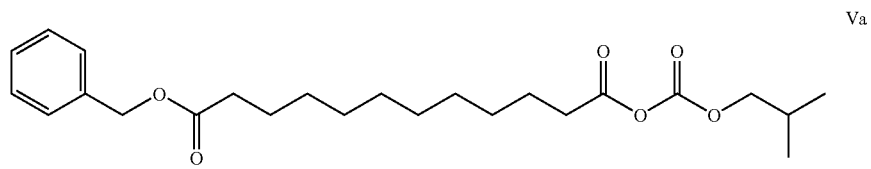

and,
b) reacting the compound of formula Va with a compound of formula IV to form the compound of formula VIII.

Also provided is a process for preparing a compound of formula I

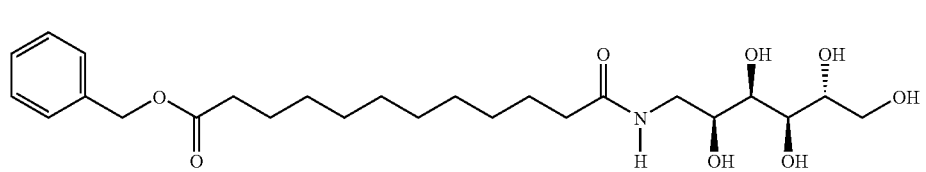

comprising reacting a compound of formula VIII

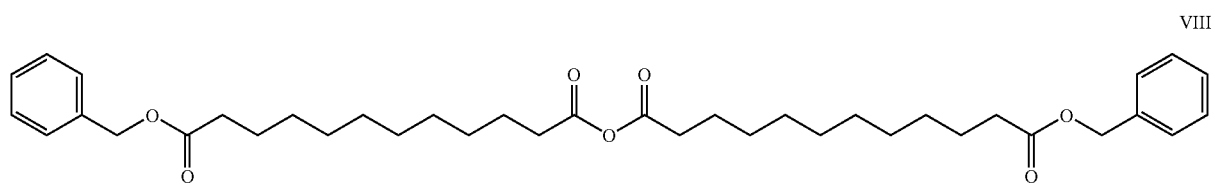

with D-glucamine to form the compound of formula I.

Also provided is a compound of formula I

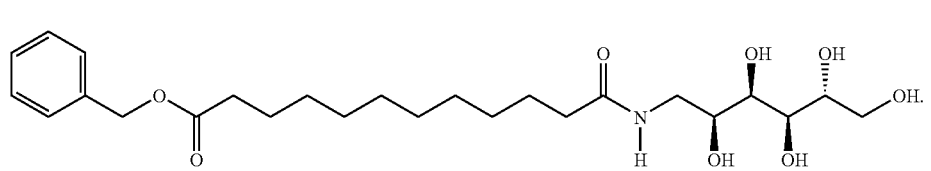

Also provided is a compound of formula A

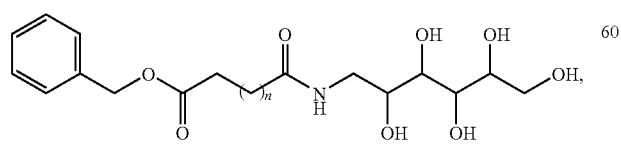

wherein n is an integer from 6 to 17.

Also provided is a compound of formula V

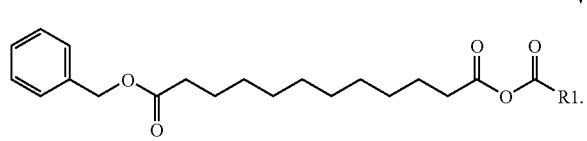

Also provided is a compound of formula Va

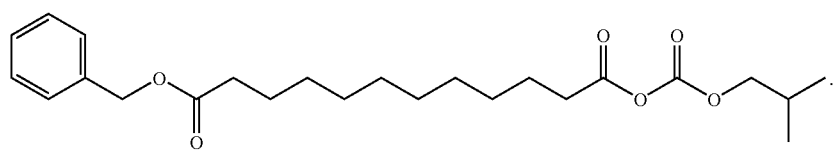

Also provided is a compound of formula VIII

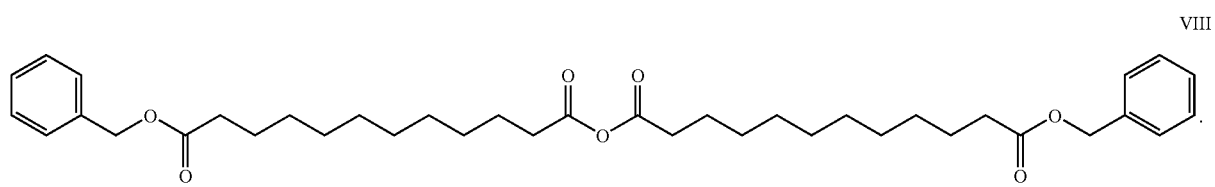

Other aspects and embodiments will be apparent to those skilled in the art from the following detailed description.

As used herein, the following words and phrases are generally intended to have the meanings as set forth below, except to the extent that the context in which they are used indicates otherwise.

As used herein, an alkyl radical is a straight-chain or branched hydrocarbon chain having from one to eighteen carbon atoms, e.g. methyl, ethyl, isopropyl, n-butyl, isobutyl, tert-butyl, hexyl, heptyl, octyl.

As used herein, an aryl radical is a phenyl, naphthyl, or biphenyl radical in which at least one CH group is optionally replaced by O, N, or S. The aryl radicals are optionally substituted by at least one suitable group, e.g.: F, Cl, Br, I, $CF_3$, $NO_2$, CN, $COO(C_1\text{-}C_6)$alkyl, $CON[(C_1\text{-}C_6)\text{alkyl}]_2$, cycloalkyl, $(C_1\text{-}C_{10})$-alkyl, $(C_2\text{-}C_6)$-alkenyl, $(C_2\text{-}_6)$-alkynyl, $O-(C_1\text{-}C_6)$-alkyl, $O-(C_2\text{-}C_6)$-alkenyl, $O-(C_2\text{-}C_6)$-alkynyl, $O-CO-(C_1\text{-}C_6)$-alkyl, $O-CO-(C_1\text{-}C_6)$-aryl, $O-CO-(C_1\text{-}C_6)$-heterocycle, $SO_2N[(C_1\text{-}C_6)\text{-alkyl}]_2$, $S-(C_1\text{-}C_6)$-alkyl, $N((C_1\text{-}C_6)\text{-alkyl})_2$.

As described herein, "glucamine" refers to a compound according to the formula:

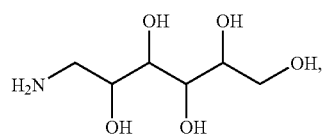

a stereoisomer thereof, or a salt thereof. A specific glucamine is D-glucamine represented by the formula:

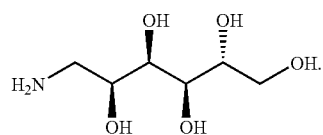

As used herein, the term "reacting" is intended to represent bringing the chemical reactants together under conditions such as to cause the chemical reaction indicated to take place.

As use herein, the term "converting" is intended to represent changing one compound into another, for example converting a compound of formula I into a compound of formula II.

The compounds described herein may be present in crystalline or amorphous solid forms. Those crystalline forms may include polymorphs and solvates, such as hydrates.

Provided is a process for preparing a compound of formula I

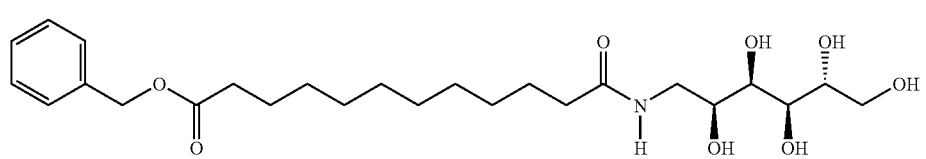

comprising
a) reacting a compound of formula IV

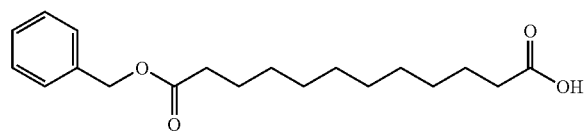

with a compound of formula VI

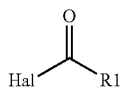

wherein
Hal is chosen from Br, Cl, and I, and
R1 is an alkyl radical which has from 1 to 18 carbon atoms and in which
at least one —CH$_2$— group of the alkyl radical is optionally replaced by at least one group chosen from —O—, —CO—, —CH=CH—, —C≡C—, and aryl groups, and
the alkyl radical is optionally substituted by at least one halogen chosen from F, Cl, Br, and I,
to form a compound of formula V

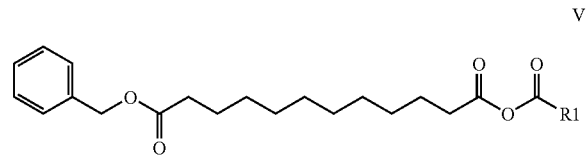

and
b) reacting the compound of formula V with D-glucamine to form the compound of formula I.

In some exemplary embodiments, the compound of formula VI is chosen from alkylcarboxylic halides and alkyl haloformates. In some exemplary embodiments, the compound of formula VI is isobutyl chloroformate.

In some exemplary embodiments, Hal is Cl.

In some exemplary embodiments, R1 is chosen from methyl, ethyl, propyl, isopropyl, butyl, isobutyl, tert-butyl, methyloxy, ethyloxy, propyloxy, isopropyloxy, butyloxy, isobutyloxy, tert-butyloxy, and benzyloxy. In some exemplary embodiments, R1 is isobutyloxy.

In some exemplary embodiments, in step a), the compound of formula IV is dissolved in a suitable solvent or solvent mixture in the presence of a suitable base at from −30° C. to 70° C., such as from −10° C. to 40° C., further such as from −5° C. to 0° C. A compound of formula IV may be added over a period of 30-150 minutes, such as 60-120 minutes, to a solution of a compound of formula VI. In some exemplary embodiments, the solution of a compound of formula VI may be cooled to from −10° C. to 30° C., such as from −10 to 0° C.

In some exemplary embodiments, in step a), a solution of a compound of formula VI in a suitable solvent or solvent mixture which is cooled to from −10° C. to 30° C., such as from −10° C. to 0° C., is added to a compound of formula IV and a suitable base in a suitable solvent or solvent mixture at from −30° C. to 70° C., such as from −10° C. to 40° C., further such as from −5° C. to 0° C., over a period of 30-150 minutes, such as 60-120 minutes.

In some exemplary embodiments, in step a), the reaction mixture is stirred at from −10° C. to 40° C., such as from −10° C. to 0° C., for from 15-150 minutes, such as 30-120 minutes. The reaction mixture may then either be used directly in the subsequent reaction or the product formed is isolated. In some exemplary embodiments, the reaction mixture is used directly. In some exemplary embodiments, the compound of formula V is isolated by evaporation of the solvent(s) under reduced pressure. In some exemplary embodiments, the reaction mixture is washed with water before the evaporation.

In some exemplary embodiments, the suitable base used in step a) is chosen from tertiary amines such as triethylamine, ethyldimethylamine, ethyldiisopropylamine, tributylamine, N-ethylmorpholine, tetramethylethylenediamine, guanidine, and alkyl guanidines. In some exemplary embodiments, the suitable base is chosen from triethylamine and ethyldiisopropylamine.

In some exemplary embodiments, the suitable solvent used in step a) is chosen from aprotic organic solvents such as toluene, chlorobenzene, dichloromethane, ethyl acetate, butyl acetate, diisobutyl ether, diisopropyl ether, tetrahydrofuran, 2-methyltetrahydrofuran, dimethylformamide, N-methylpyrrolidone, and methyl ethyl ketone. In some exemplary embodiments, the suitable solvent is chosen from ethyl acetate and butyl acetate. In some exemplary embodiments, a mixture of solvents is used.

In some exemplary embodiments, in step b), D-glucamine is added a little at a time over a period of from 5-60 minutes, such as 15-30 minutes, to a solution of a compound of formula V and a suitable base in a suitable solvent or solvent mixture at from −10° C. to 40° C., such as from −5° C. to 0° C.

In some exemplary embodiments, the suitable base used in step b) is chosen from tertiary amines such as triethylamine, ethyldimethylamine, ethyldiisopropylamine, tributylamine, N-ethylmorpholine, tetramethylethylenediamine, guanidine, and alkyl guanidines. In some exemplary embodiments, the suitable base is chosen from triethylamine and ethyldiisopropylamine.

In some exemplary embodiments, the suitable solvent used in step b) is chosen from aprotic organic solvents such as toluene, chlorobenzene, dichloromethane, ethyl acetate, butyl acetate, diisobutyl ether, diisopropyl ether, tetrahydrofuran, 2-methyltetrahydrofuran, dimethylformamide, N-methylpyrrolidone, and methyl ethyl ketone. In some embodiments, the suitable solvent is chosen from ethyl acetate and butyl acetate. In some exemplary embodiments, a mixture of solvents is used.

In some exemplary embodiments, the reaction mixture of step b) is stirred for a further period of from 5-120 minutes, such as 30-60 minutes, at from −10° C. to 40° C., such as from −5° C. to 0° C., subsequently for a further 5-20 hours, such as 12 hours, at from 0 to 30° C., such as from 15° C. to 20° C., and subsequently washed with water at 10° C. to 80° C., such as 50° C. to 70° C., and further such as 60° C. The mixture is subsequently cooled to a temperature sufficient to induce crystallization of the compound of formula I, such as 20° C. In some exemplary embodiments, the compound of formula I is purified by recrystallization.

Also provided is a process for preparing a compound of formula I with a compound of formula VI

wherein Hal is chosen from Br, Cl, and I, and

R1 is an alkyl radical which has from 1 to 18 carbon atoms and in which at least one —CH$_2$— group of the alkyl radical is optionally replaced by at least one group chosen from —O—, —CO—, —CH═CH—, —C≡C—, and aryl groups, and the alkyl radical is optionally substituted by at least one halogen chosen from F, Cl, Br, and I,

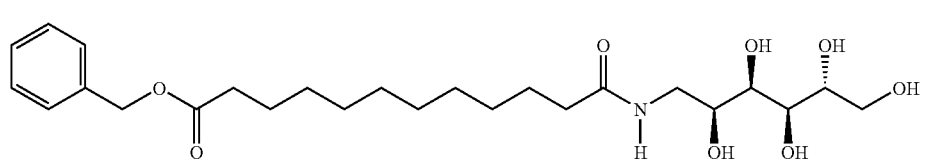

comprising a) reacting a compound of formula IV

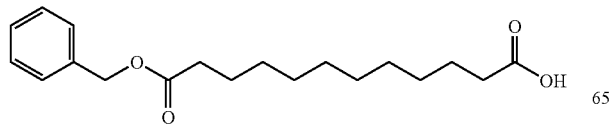

to form a compound of formula V

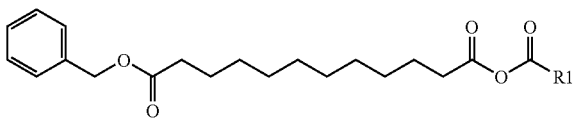

b) reacting the compound of formula V with the compound of formula IV to form a compound of formula VIII furan, 2-methyltetrahydrofuran, dimethylformamide, N-methylpyrrolidone, or methyl ethyl ketone. In some exemplary In some exemplary embodiments, the suitable solvent used in step a) is chosen from customary organic solvents such as toluene, chlorobenzene, dichloromethane, ethyl acetate, butyl acetate, diisobutyl ether, diisopropyl ether, tetrahydro pylamine. embodiments, the suitable solvent is ethyl acetate or butyl acetate. In some exemplary embodiments, a mixture of solvents is used.

In some exemplary embodiments, in step b), the compound of formula IV is added a little at a time to a solution of product V and optionally a suitable base in a suitable solvent or solvent mixture at from −10° C. to 40° C., such as from 0° C. to 25° C., over a period of 5-60 minutes, such as 15-30 minutes.

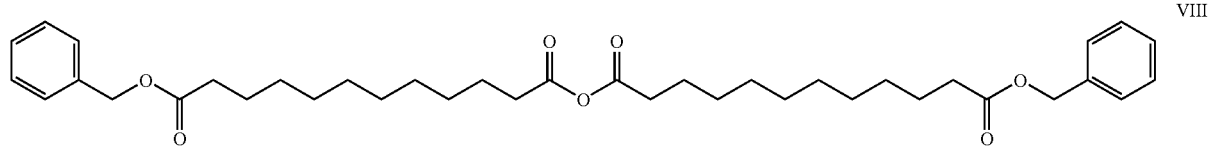

and c) reacting the compound of formula VIII with D-glucamine to form the compound of formula I.

In some exemplary embodiments, the compound of formula VI is chosen from alkylcarboxylic halides and alkyl haloformates. In some exemplary embodiments, the compound of formula VI is isobutyl chloroformate.

In some exemplary embodiments, Hal is Cl.

In some exemplary embodiments, R1 is chosen from methyl, ethyl, propyl, isopropyl, butyl, isobutyl, tert-butyl, methyloxy, ethyloxy, propyloxy, isopropyloxy, butyloxy, isobutyloxy, tert-butyloxy, and benzyloxy. In some exemplary embodiments, R1 is isobutyloxy.

In some exemplary embodiments, in step a), the compound of formula IV is dissolved in a suitable solvent or solvent mixture in the presence of at least one base at from −30° C. to 70° C., such as from −10° C. to 40° C., further such as from −5° C. to 0° C., and added over a period of 30-150 minutes, such as 60-120 minutes, to a solution of compound of formula VI which is cooled to from −10° C. to 30° C., such as from −10 to 0° C.

In some exemplary embodiments, in step a), a solution of a compound of formula VI in a suitable solvent or solvent mixture is cooled to from −10° C. to 30° C., such as from −10° C. to 0° C., in a reaction vessel and then is added to a compound of formula IV and a suitable base in a suitable solvent or solvent mixture at from −30° C. to 70° C., such as from −10° C. to 40° C., further such as from −5° C. to 0° C., over a period of 30-150 minutes, such as 60-120 minutes.

In some exemplary embodiments, the reaction mixture in step a) is stirred at from −10° C. to 40° C., such as from −10° C. to 0° C., for from 15-150 minutes, such as 30-120 minutes. The reaction mixture can then either be used directly in the subsequent reaction or the product formed is isolated. In some exemplary embodiments, the reaction mixture is used directly. In some exemplary embodiments, the compound of formula V is isolated by evaporation under reduced pressure. In some exemplary embodiments, the reaction mixture is washed with water before the evaporation.

In some exemplary embodiments, the suitable base used in step a) is chosen from tertiary amines such as triethylamine, ethyldimethylamine, ethyldiisopropylamine, tributylamine, N-ethylmorpholine, tetramethylethylenediamine, guanidine, and alkyl guanidines. In some exemplary embodiments, the suitable base is chosen from triethylamine and ethyldiisopro- In some exemplary embodiments, the suitable base used in step b) is chosen from tertiary amines such as triethylamine, ethyldimethylamine, ethyldiisopropylamine, tributylamine, N-ethylmorpholine, tetramethylethylenediamine, guanidine, and alkyl guanidines. In some exemplary embodiments, the suitable base is chosen from triethylamine and ethyldiisopropylamine.

In some exemplary embodiments, the suitable solvent used in step b) is chosen from aprotic organic solvents such as toluene, chlorobenzene, dichloromethane, ethyl acetate, butyl acetate, diisobutyl ether, diisopropyl ether, tetrahydrofuran, 2-methyltetrahydrofuran, dimethylformamide, N-methylpyrrolidone, and methyl ethyl ketone. In some exemplary embodiments, the suitable solvent is chosen from ethyl acetate and butyl acetate. In some exemplary embodiments, a mixture of solvents is used.

In some exemplary embodiments, the reaction mixture of step b) is stirred at from −10° C. to 40° C., such as from 0° C. to 25° C., for another 5-240 minutes, such as 60-150 minutes. In some exemplary embodiments, the precipitate formed is filtered and dried, giving a compound of formula VIII.

In some exemplary embodiments, in step c), D-glucamine is added a little at a time to a solution of product VIII and optionally a suitable base in a suitable solvent or solvent mixture at from −10° C. to 40° C., such as from −5° C. to 5° C., over a period of from 5-60 minutes, such as 15-30 minutes.

In some exemplary embodiments, the suitable base used in step c) is chosen from tertiary amines such as triethylamine, ethyldimethylamine, ethyldiisopropylamine, tributylamine, N-ethylmorpholine, tetramethylethylenediamine, guanidine, and alkyl guanidines. In some exemplary embodiments, the suitable base is chosen from triethylamine and ethyldiisopropylamine.

In some exemplary embodiments, the suitable solvent used in step c) is chosen from aprotic organic solvents such as toluene, chlorobenzene, dichloromethane, ethyl acetate, butyl acetate, diisobutyl ether, diisopropyl ether, tetrahydrofuran, 2-methyltetrahydrofuran, dimethylformamide, N-methylpyrrolidone, and methyl ethyl ketone. In some exemplary embodiments, the suitable solvent is chosen from ethyl acetate and butyl acetate. In some exemplary embodiments, a mixture of solvents is used.

In some exemplary embodiments, the reaction mixture in step c) is stirred at from −10° C. to 40° C., such as from 10° C. to 25° C., for another 1-20 hours, such as 10-18 hours, and subsequently washed with water at 10° C. to 80° C., such as 50° C. to 70° C. The mixture is subsequently cooled to a temperature sufficient to induce crystallization of the compound of formula I, such as 20° C. In some exemplary embodiments, the compound of formula I is purified by recrystallization.

In some exemplary embodiments, the compound of formula I, which may be obtained as described herein, is converted into a compound of formula II

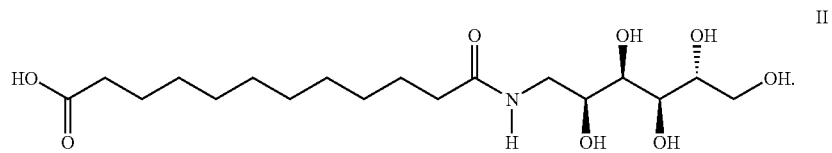

In some exemplary embodiments, converting the compound of formula I into a compound of formula II comprises reacting the compound of formula I under alkaline conditions, using, for example, aqueous sodium hydroxide or aqueous potassium hydroxide.

In some embodiments, converting the compound of formula I into a compound of formula II comprises reacting the compound of formula I under enzymatic conditions to form formula II. Non-limiting examples of suitable enzymes include lipases, for example *Candida*.

In some exemplary embodiments, converting the compound of formula I into a compound of formula II comprises hydrogenating the compound of formula I under suitable conditions.

In some exemplary embodiments, hydrogenating the compound of formula I comprises reacting the compound of formula I with a hydrogen source in the presence of a hydrogenation catalyst. In some exemplary embodiments, a hydrogenation catalyst, such as palladium on carbon (Pd/C), Raney-Nickel, platinum, platinum oxide, or zinc oxide is used. In some exemplary embodiments, the hydrogen source is chosen from hydrogen gas and ammonium formate.

Also provided is a process for preparing a compound of formula III comprising a) reacting a compound of formula IV

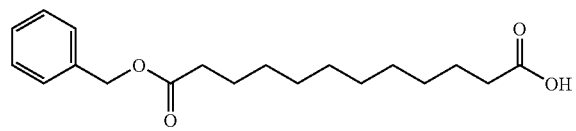

with a compound of formula VI

wherein Hal is chosen from Br, Cl, and I, and

R1 is an alkyl radical which has from 1 to 18 carbon atoms and in which at least one —CH$_2$— group of the alkyl radical is optionally replaced by at least one group chosen from —O—, —CO—, —CH=CH—, —C≡C—, and aryl groups, and the alkyl radical is optionally substituted by at least one halogen chosen from F, Cl, Br, and I, to form a compound of formula V

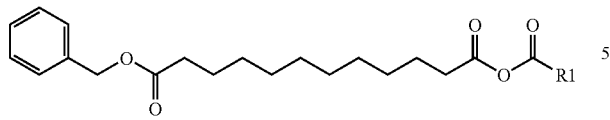

V b) reacting the compound of formula V with D-glucamine to form the compound of formula I

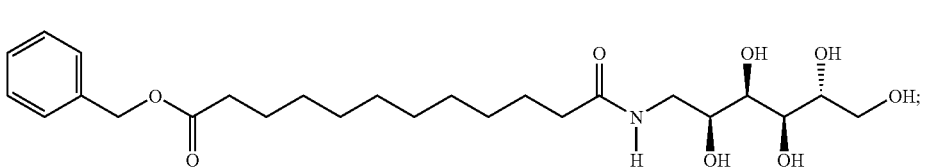

I c) converting the compound of formula I into a compound of formula II

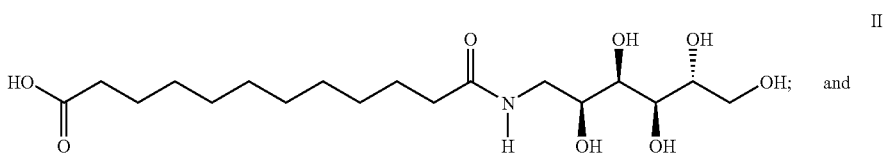

II and d) reacting the compound of formula II with a compound of formula VII

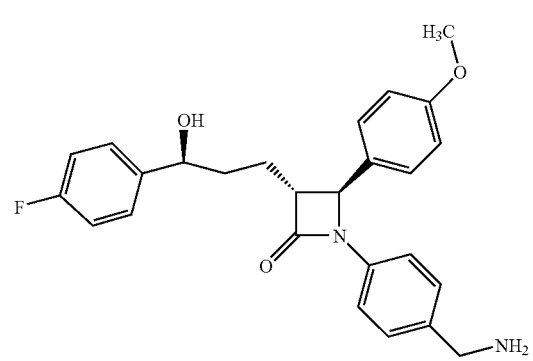

VII to form a compound of formula III.

In some exemplary embodiments, the reaction conditions for the preparation of a compound of formula V, a compound of formula I, and a compound of formula II are as described herein.

In some exemplary embodiments, reacting the compound of formula II with a compound of formula VII comprises reacting the compound of formula II with suitable peptide coupling reagents in a suitable solvent or solvent mixture, and then further reacting with a compound of formula VII. Suitable peptide coupling reagents and solvents or solvent mixtures are described, inter alia, in, for example, A. Speicher et al. In Journal für Praktische Chemie/Chemiker-Zeitung (1998), 340, 581-583; Y. S. Klausner and M. Bodansky, Synthesis, (1972), 453 et. seq.; K. Ishihara et al., J. Org. Chem., 61, 4196 (1996); M. Kunishima et al., Tetrahedron 55, 13159-13170 (1999), or R. C. Larock: Comprehensive Organic Transformations; VCH, New York, 1989, page 981 et. seq.

The reaction of the compound of formula II with the amine of formula VII is described, for example, in WO 02/50027 or U.S. Pat. No. 7,205,290.

Also provided herein is a process for preparing a compound of formula III

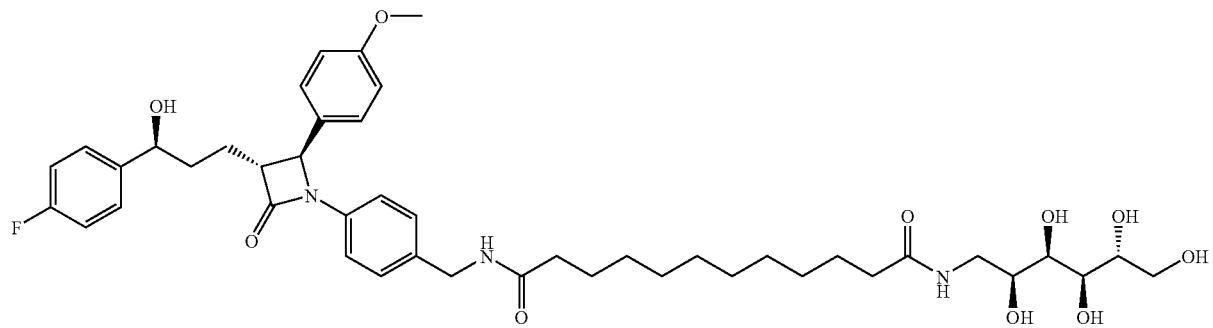

comprising
a) reacting a compound of formula IV

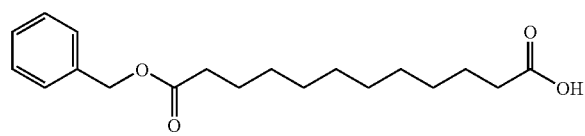

with a compound of formula VI

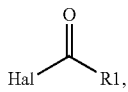

wherein Hal is chosen from Br, Cl, and I, and
R1 is an alkyl radical which has from 1 to 18 carbon atoms and in which at least one —CH$_2$— group of the alkyl radical is optionally replaced by at least one group chosen from —O—, —CO—, —CH=CH—, —C≡C—, and aryl groups, and
the alkyl radical is optionally substituted by at least one halogen chosen from F, Cl, Br, and I,
to form a compound of formula V

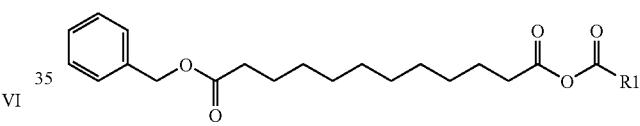

b) reacting the compound of formula V with monobenzyl ester of dodecanedioic acid of formula IV to form a compound of formula VIII

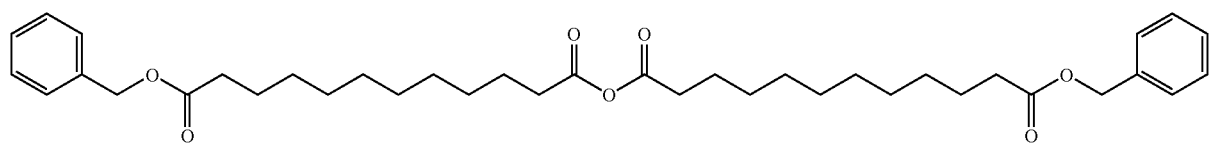

c) reacting the compound of formula VIII with D-glucamine to form the compound of formula I

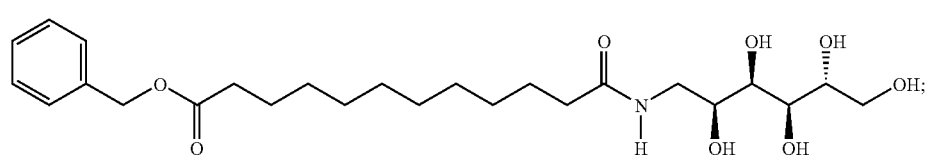

d) converting the compound of formula I into a compound of formula II

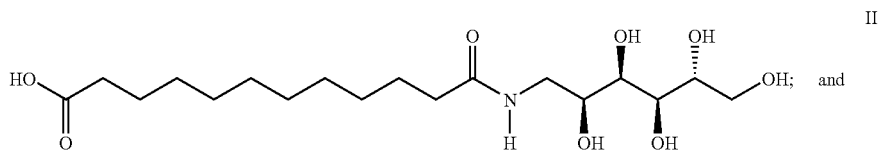

e) reacting the compound of formula II with a compound of formula VII

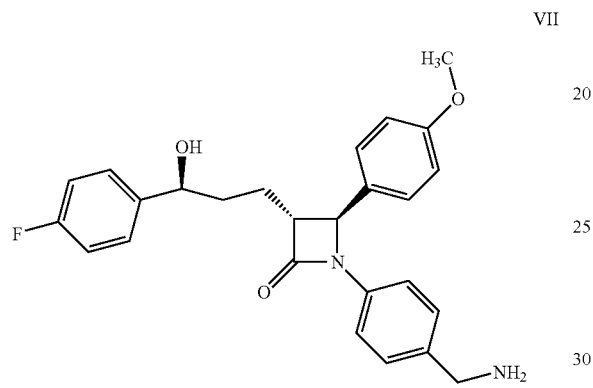

to form a compound of formula III.

In some exemplary embodiments, the reaction conditions for the preparation of a compound of formula V, a compound of formula VIII, a compound of formula I, a compound of formula II, and a compound of formula III are as described herein.

Also provided is a process of preparing a compound of formula I

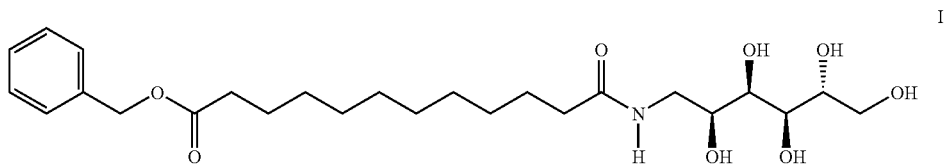

comprising converting a compound of formula V

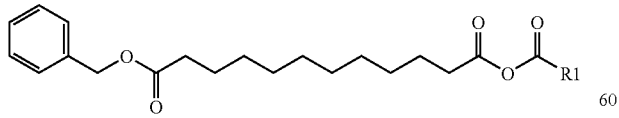

to the compound of formula I.

In some exemplary embodiments, the reaction conditions for the preparation of a compound of formula I from a compound of formula V are as described herein.

Also provided is a process of preparing a compound of formula I

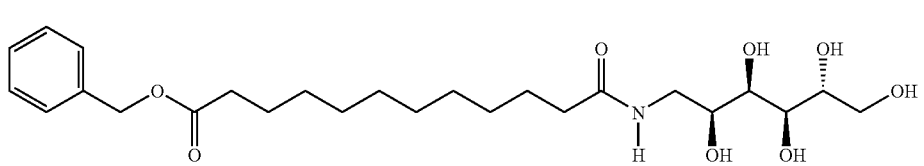

comprising converting a compound of formula Va

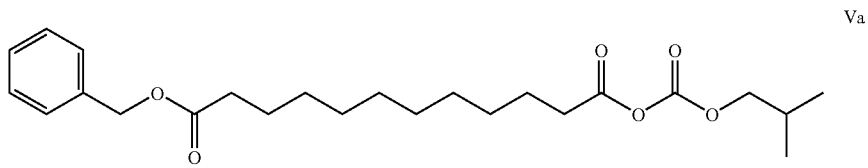

to the compound of formula I.

In some exemplary embodiments, the reaction conditions for the preparation of a compound of formula I from a compound of formula Va are as described herein.

Also provided is a process for preparing a compound of formula Va

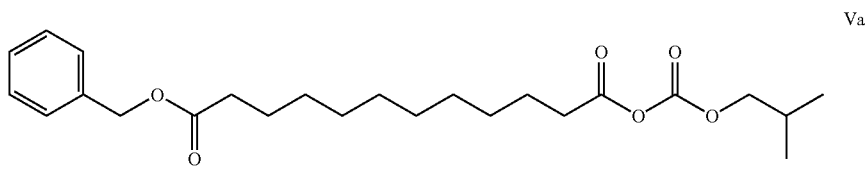

comprising reacting a compound of formula IV

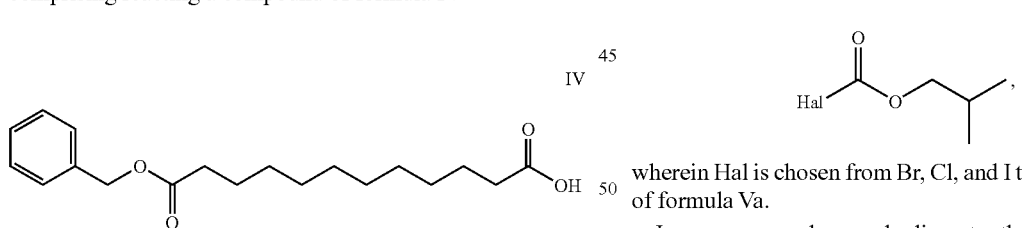

with a compound of formula VIa wherein Hal is chosen from Br, Cl, and I to form a compound of formula Va.

In some exemplary embodiments, the processes for the preparation of a compound of formula Va from a compound of formula IV are as described herein.

Also provided is a process for preparing a compound of formula I

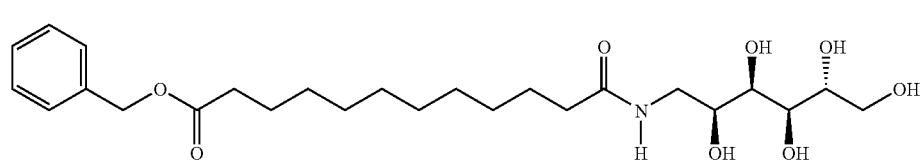

comprising reacting a compound of formula Va

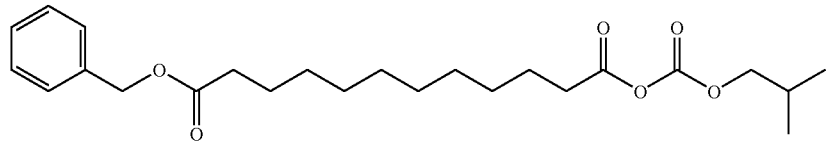

with D-glucamine to form the compound of formula I.

In some exemplary embodiments, the reaction conditions for the preparation of a compound of formula I from a compound of formula Va are as described herein.

Also provided is a process for preparing a compound of formula VIII

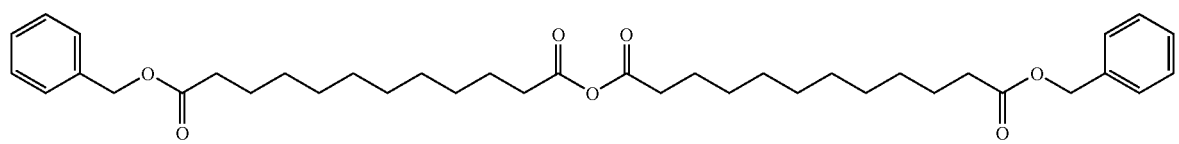

comprising
a) reacting a compound of formula IV

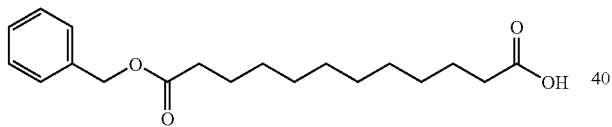

with a compound of formula VIa

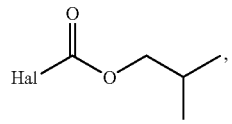

wherein Hal is chosen from Br, Cl, and I,
to form a compound of formula Va

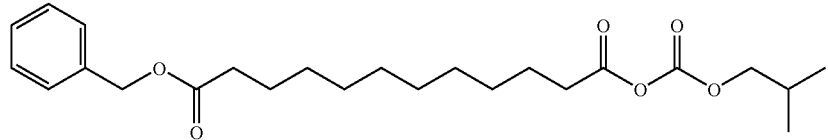

and,
b) reacting the compound of formula Va with the compound of formula IV to form the compound of formula VIII.

In some exemplary embodiments, the reaction conditions for the preparation of a compound of formula Va from a compound of formula IV and for the preparation of a compound of formula VIII from a compound of formula Va are as described herein.

Also provided is a process for preparing a compound of formula I

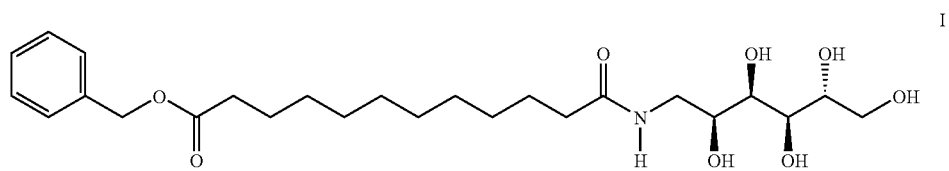

comprising reacting a compound of formula VIII

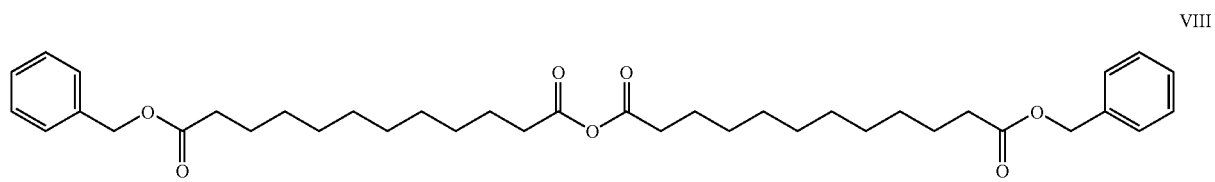

with D-glucamine to form the compound of formula I.

In some exemplary embodiments, the reaction conditions for the preparation of a compound of formula I from a compound of formula VIII are as described herein.

Also provided is a compound of formula Va.

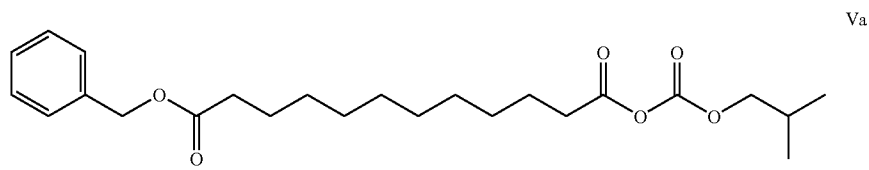

Also provided is a compound of formula VIII.

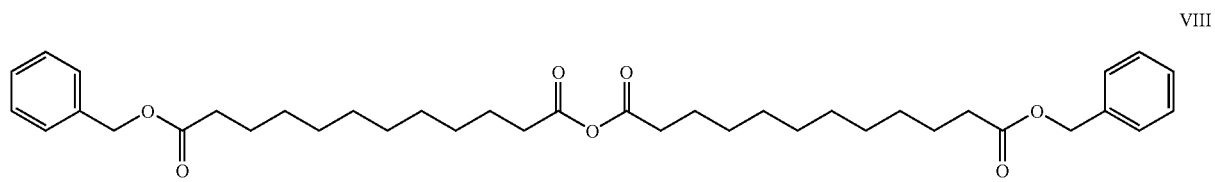

EXAMPLES

The following examples serve to more fully describe the manner of using the invention. These examples are presented for illustrative purposes and should not serve to limit the true scope of the invention.

1. Preparation of benzyl 12-isobutoxycarbonyloxy-12-oxododecanoate (Va)

1.5 g (4.7 mmol) of the monobenzyl ester of dodecanedioic acid together with 15 ml of ethyl acetate are placed in a reaction vessel and admixed with 0.8 ml (5.6 mmol) of triethylamine. The mixture is cooled to −5° C. and a solution of 0.7 ml (5.0 mmol) of isobutyl chloroformate is added. After 60 minutes, the precipitate is filtered off with suction under protective gas, washed twice with ethyl acetate, and the filtrate is evaporated to dryness to obtain benzyl 12-isobutoxycarbonyloxy-12-oxododecanoate (Va).

2. Preparation of benzyl 11-(2S,3R,4R,5R-2,3,4,5,6-pentahydroxyhexylcarbamoyl)undecanoate I from benzyl 12-isobutoxycarbonyloxy-12-oxododecanoate (Va)

Benzyl 12-isobutoxycarbonyloxy-12-oxododecanoate is dissolved in 15 ml of ethyl acetate and admixed at 0° C. with 0.9 g (5.2 mmol) of 2R,3R,4R,5S-6-aminohexane-1,2,3,4,5-pentanol (D-glucamine). The mixture is stirred at 0° C. for one hour, warmed to 20° C. and allowed to stand overnight. The white suspension formed is shaken three times at 65° C. with 20 ml of water at the same temperature. The organic phase is subsequently evaporated to dryness to obtain benzyl 11-(2S,3R,4R,5R-2,3,4,5,6-pentahydroxyhexylcarbamoyl)undecanoate (I).

3. Preparation of the anhydride of dodecanedicarboxylic monobenzyl ester (VIII) from benzyl 12-isobutoxycarbonyloxy-12-oxododecanoate (Va)

Benzyl 12-isobutoxycarbonyloxy-12-oxododecanoate is admixed with 20 ml of ethyl acetate and admixed at 20° C. with 1.9 g (4.2 mmol) of the monobenzyl ester of dodecanedioic acid. The mixture is stirred for 2.5 hours, and the precipitate formed is filtered off and dried to obtain anhydride of dodecanedicarboxylic monobenzyl ester (VIII).

4. Preparation of benzyl 11-(2S,3R,4R,5R-2,3,4,5,6-pentahydroxyhexylcarbamoyl)undecanoate (I) from the anhydride of dodecanedioic acid monobenzyl ester (VIII)

0.50 g (0.80 mmol) of the anhydride of dodecanedioic acid monobenzyl ester (VIII) together with 10 ml of ethyl acetate are placed in a reaction vessel and admixed with 0.14 ml (0.96 mmol) of triethylamine and the mixture is cooled to 0° C. A suspension of 0.16 g (0.88 mmol) of 2R,3R,4R,5S-6-aminohexane-1,2,3,4,5-pentanol (D-glucamine) in 6 ml of ethyl acetate is added and the mixture is stirred at room temperature for 18 hours. The mixture is heated to 70° C. and shaken three times with 20 ml of water at the same temperature. The organic phase is allowed to cool to room temperature, and the precipitate formed is filtered off and dried to obtain benzyl 11-(2S,3R,4R,5R-2,3,4,5,6-pentahydroxyhexylcarbamoyl)undecanoate (I).

5. Preparation of benzyl 11-(2S,3R,4R,5R-2,3,4,5,6-pentahydroxyhexylcarbamoyl)undecanoate (I) from the monobenzyl ester of dodecanedioic Acid (IVa) without Isolation of the Intermediates 17 kg of isobutyl chloroformate together with 150 L of ethyl acetate are placed in a reaction vessel and cooled to −5° C. A solution of 37.3 kg of the monobenzyl ester of dodecanedioic acid and 14.2 kg of triethylamine in 100 L of ethyl acetate which has been cooled to −5° C. is added to the above solution over a period of 2 hours. After the addition is complete to form a compound of formula Va, the mixture is stirred at −5° C. for another 2 hours. 23.2 kg of D-glucamine are then added a little at a time at −5° C. over a period 30 minutes and, after the addition is complete, the mixture is stirred at −5° C. for another 1 hour and subsequently at 20° C. for 12 hours. The reaction mixture is poured into 200 L of ethyl acetate and 300 L of water, the mixture is heated to 65° C., and the phases are separated. The organic phase is washed at 60° C. with a further 80 L of water and the organic phase is subsequently cooled to 20° C. over a period of 60 minutes. After stirring for another 1 hour, the precipitated solid is filtered off and dried to obtain benzyl 11-(2S,3R,4R,5R-2,3,4,5,6-pentahydroxyhexylcarbamoyl)undecanoate (I).

Subsequent experiments produced a compound of formula (II) from a compound of formula (I) under various conditions, including basic reaction conditions, enzymatic reaction conditions, and hydrogenation reaction conditions, utilizing Pd/C and hydrogen, and experiments were also performed to further produce from a compound of formula (II) a compound of formula (III), which has use for treating hyperlipidemia and arteriosclerosis and hypercholesterolemia as described in U.S. Pat. No. 7,205,290.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step, or steps, and all such modifications are intended to be within the scope of the claims appended hereto.

The invention claimed is:

1. A compound of formula V

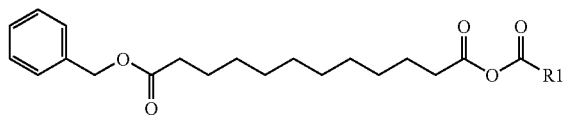

where R1 is an alkyl radical which has from 1 to 18 carbon atoms and in which at least one —CH$_2$— group of the alkyl radical is optionally replaced by at least one group chosen from —O—, —CO—, —CH═CH—, —C≡C—, and aryl groups and the alkyl radical is optionally substituted by at least one halogen chosen from F, Cl, Br, and I.

2. A compound of claim 1 of formula Va
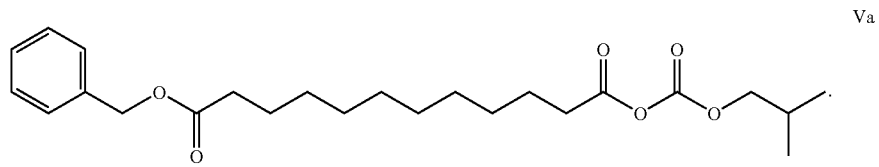
3. A compound of claim 1 of formula VIII
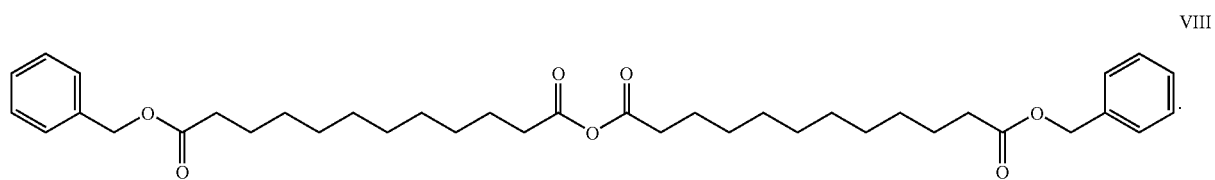
* * * * *